United States Patent

Milner

[11] Patent Number: 4,661,480
[45] Date of Patent: Apr. 28, 1987

[54] FORMAMIDO OXACEPHEMS

[75] Inventor: Peter H. Milner, Horsham, England

[73] Assignee: Beecham Group p.l.c., England

[21] Appl. No.: 572,186

[22] Filed: Jan. 19, 1984

[30] Foreign Application Priority Data

Jan. 21, 1983 [GB] United Kingdom ............... 8301692
Jul. 9, 1983 [GB] United Kingdom ............... 8318619
Jul. 30, 1983 [GB] United Kingdom ............... 8320593

[51] Int. Cl.$^4$ ............... A61K 31/535; C07D 498/04
[52] U.S. Cl. ............................... 514/210; 544/90
[58] Field of Search ............ 544/90; 424/248.51, 424/248.54; 514/210

[56] References Cited

U.S. PATENT DOCUMENTS

| 4,200,576 | 4/1980 | Feyen et al. | 544/90 |
| 4,226,866 | 10/1980 | Christensen et al. | 544/90 |
| 4,232,151 | 4/1980 | Nagata et al. | 544/90 |
| 4,399,135 | 8/1983 | Farge et al. | 544/90 |

Primary Examiner—Glennon H. Hollrah
Assistant Examiner—D. L. Dinner
Attorney, Agent, or Firm—Jacobs & Jacobs

[57] ABSTRACT

A compound of formula (I) or a pharmaceutically acceptable salt or in vivo hydrolyzable ester thereof:

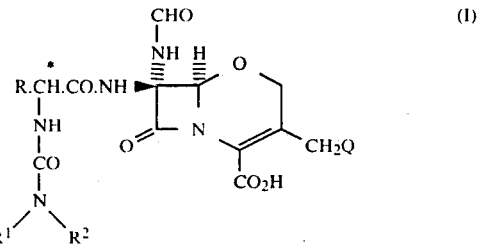

R is phenyl, substituted phenyl, $C_{3-6}$ cycloalkyl cyclohexenyl, cyclohexadienyl, or a 5- or 6-membered heterocyclic ring containing up to three hetero-atoms slected from oxygen, sulphur or nitrogen, optionally substituted with hydroxy, amino, halogen, substituted amino or $C_{1-6}$ alkoxy; Q represents acetoxy, carbamoyloxy, heterocyclylthio group, or a nitrogen containing heterocyclic group bonded via nitrogen; $R^1$ is hydrogen or a $C_{1-6}$ alkyl group and $R^2$ is an optionally substituted 5- or 6-membered heterocyclic group containing one or two heteroatoms; or $R^1$ and $R^2$ together with the nitrogen atom to which they are attached form an optionally substituted five- or six-membered heterocyclic group containing one or two nitrogen heteroatoms; a process for the preparation of such compounds and pharmaceutical compositions comprising them.

12 Claims, No Drawings

FORMAMIDO OXACEPHEMS

This invention relates to a class of oxadethiacephem derivatives which have antibacterial activity and are of value in the treatment of infections in animals, especially mammals including man, caused by a wide range of organisms, particularly Gram-negative organisms. In particular the invention relates to a class of 6α-formamidyl oxadethiacephem derivatives. The invention also relates to a process for the preparation of such compounds, and to pharmaceutical compositions comprising them.

According to the present invention there is provided a compound of formula (I) or a pharmaceutically acceptable salt or in vivo hydrolysable ester thereof:

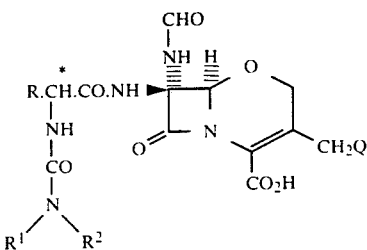

R is phenyl, substituted phenyl, $C_{3-6}$ cycloalkyl cyclohexenyl, cyclohexadienyl, or a 5- or 6-membered heterocyclic ring containing up to three hetero-atoms selected from oxygen, sulphur or nitrogen, optionally substituted with hydroxy, amino, halogen, substituted amino or $C_{1-6}$ alkoxy; Q represents acetoxy, carbamoyloxy, heterocyclylthio group, or a nitrogen containing heterocyclic group bonded via nitrogen; $R^1$ is hydrogen or a $C_{1-6}$ alkyl group and $R^2$ is an optionally substituted 5- or 6- membered heterocyclic group containing one or two heteroatoms; or $R^1$ and $R^2$ together with the nitrogen atom to which they are attached form an optionally substituted five- or six-membered heterocyclic group containing one or two nitrogen heteroatoms.

The carbon atom marked * in formulae herein is asymmetric so that the compounds may exist as two optically active diastereoisomers. In general that prepared from the D-side chain exhibits the highest antibacterial activity and accordingly the D compound or the DL mixtures are preferred, with the D compound being particularly preferred.

Suitable pharmaceutically acceptable salts of the compound of formula (I) include metal salts e.g. aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)-amine, cycloalkylamines such as dicyclohexylamine, or with procaine, dibenzylamine, N,N-dibenzylethylene-diamine, 1-ephenamine, N-ethylpiperidine, N-benzyl-β-phenethylamine, dehydroabietylamine, N,N'-bisdehydroabietylamine, ethylenediamine, or bases of the pyridine type such as pyridine, collidine or quinoline, or other amines which have been used to form salts with known penicillins and cephalosporins. Other suitable salts include the lithium and silver salt.

Examples of suitable pharmaceutically acceptable in vivo hydrolysable esters of compound (I) include those which break down readily in the human body to leave the parent acid or its salt. Suitable ester groups of this type include those of part formula (i), (ii) and (iii):

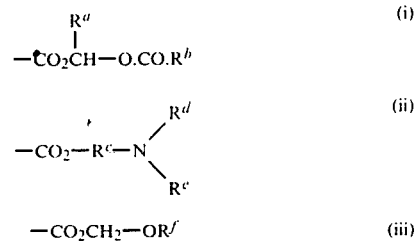

wherein $R^a$ is hydrogen, methyl, or phenyl, $R^b$ is $C_{1-6}$ alkyl, $C_{1-6}$ alkoxy or phenyl; or $R^a$ and $R^b$ together form a 1,2-phenylene group optionally substituted by one or two methoxy groups; $R^c$ represents $C_{1-6}$ alkylene optionally substituted with a methyl or ethyl group- $R^d R^d$ and $R^e$ independently represent $C_{1-6}$ alkyl; $R^f$ represents $C_{1-6}$ alkyl. Examples of suitable in vivo hydrolysable ester groups include for example acyloxyalkyl groups such as acetoxymethyl, pivaloyloxymethyl, α-acetoxyethyl and α-pivaloloxyethyl groups; alkoxycarbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

When used herein the term 'lower' suitably includes groups containing 1 to 6 carbon atoms.

Some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation.

Suitably the substituted phenyl group for R is a phenyl group substituted with up to three groups selected from $C_{1-6}$ alkyl, phenyl, halogen, $C_{1-6}$ alkoxy, amino, nitro, hydroxy, $C_{1-6}$ alkylamido, $C_{1-6}$ alkylcarbonyloxy, carboxy, $C_{1-6}$ alkoxycarbonyl, halo ($C_{1-6}$) alkyl, oxo ($C_{1-6}$) alkyl, $C_{1-6}$ alkylcarbonyl, aryloxy, aralkyloxy, arylcarbonyl, $C_{1-6}$ alkylamino or di($C_{1-6}$) alkylamino.

In formula (I) the group R is preferably phenyl, 4-hydroxyphenyl, 3,4-di($C_{1-6}$ alkylcarbonyloxy)-phenyl, 3,4-dihydroxyphenyl, 2-thienyl, 3-thienyl or 2-amino-4-thiazolyl.

Particularly preferred groups R are 3,4-dihydroxyphenyl and 3,4-diacetoxyphenyl.

Suitably $R^1$ is hydrogen.

Suitable substituents for the 5- or 6- membered heterocyclic group of $R^2$ or $R^1$ and $R^2$ together include the optionally substituted alkyl, alkenyl, alkynyl, cycloalkyl or cycloalkenyl group; optionally substituted phenyl, oxo; the hydroxy group optionally substituted by alkyl, alkenyl, cycloalkyl, phenyl, pyridyl, pyrimidyl or benzyl; the optionally substituted mercapto group, the alkylsulphonyl group; the substituted imino group; or the amino group optionally substituted by an alkyl, alkenyl, cycloalkyl, phenyl, substituted phenyl or benzyl group.

Alternatively two substituents on the ring may form the residue of a further carbocyclic or heterocyclic ring.

Suitably Q represents the heterocyclylthio group.

The heterocyclylthio group may suitably be represented by the formula:

—S—Het wherein 'Het' is a five or six membered heterocyclic ring containing from 1 to 4 atoms selected from N, O, and S unsubstituted or substituted with one or two groups selected from $C_{1-6}$ alkyl, $C_{1-6}$ alkoxy, hydroxyalkyl, $C_{1-6}$ alkenyl, alkoxyalkyl, carboxyalkyl, sulphonylalkyl, carbamoylalkyl, trifluoromethyl, hydroxy, halogen, oxo, (subst)aminoalkyl, and carboxyalkyl or two substituents may be linked to form the residue of a heterocyclic or carbocyclic ring.

Examples of the. group 'Het' include unsubstituted and substituted imidazolyl, triazolyl, tetrazolyl, thiazolyl, thiadiazolyl, thiatriazolyl, oxazolyl, triazinyl and oxadiazolyl.

Suitable groups 'Het' include unsubstituted and substituted 1,2,3-triazolyl; 1,2,4-triazolyl; tetrazolyl; oxazolyl; thiazolyl; 1,3,4-oxadiazolyl; 1,3,4-thiadiazolyl, or 1,2,4-thiadiazolyl. Preferably the heterocyclylthio group is 1-methyl-1H-tetrazol-5-ylthio, 2-methyl-1,3,4-thiadiazol-5-ylthio, 1-carboxymethyl-1H-tetrazol-5-ylthio or 6-hydroxy-2-methyl-5-oxo-2H-1,2,4-triazin-3-ylthio.

A further suitable group Q is the nitrogen containing heterocyclic group bonded via nitrogen.

The nitrogen containing heterocyclic group bonded via nitrogen is suitably a pyridinium group unsubstituted or substituted with one or two groups selected from $C_{1-6}$ alkyl, $C_{1-6}$ alkoxy, hydroxyalkyl, $C_{1-6}$ alkenyl, alkoxyalkyl, carboxyalkyl, sulphonylalkyl, carbamoylmethyl, carbamoyl, trifluoromethyl, hydroxy, halogen, and aminoalkyl.

One preferred sub-group, of compounds within the present invention provides a compound of formula (II) or hydrolysable ester thereof:

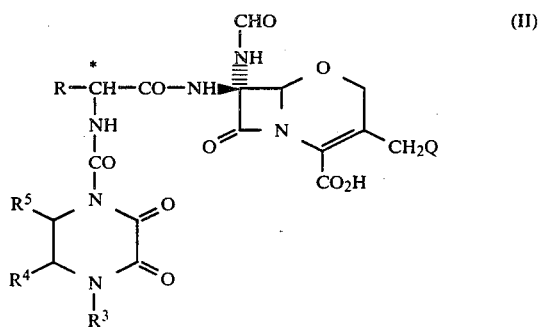

(II)

wherein R and Q are as defined with respect to formula (I) and $R^3$ represents hydrogen, $C_{1-6}$ alkyl, substituted alkyl, aryl, or aralkyl; $R^4$ and $R^5$ are the same or different and represent hydrogen, $C_{1-6}$ alkyl, substituted alkyl, halogen, amino, hydroxy or $C_{1-6}$ alkoxy or $R^4$ and $R^5$ form the residue of 5- or 6-membered carbocyclic or heterocyclic ring.

Suitable $C_{1-6}$ alkyl groups for the groups $R^3$, $R^4$ and $R^5$ in formula (II) include methyl, ethyl, n- and isopropyl, no, sec-, iso and tert-butyl. Preferably $R^3$ is ethyl. Preferably $R^4$ and $R^5$ are hydrogen.

Specific compounds within this invention include the following and pharmaceutically acceptable salts and in vivo hydrolysable esters thereof:

7β-[2-[(4-ethyl-2,3-dioxopiperazin-1-yl)carbonylamino]-2-(3,4-dihydroxyphenyl)acetamido]-7α-formamido-3-[(1-methyl-1H-tetrazol-5-yl)thiomethyl]-1-oxadethiaceph-3-em-4-carboxylic acid;

7β-[2-(3,4-diacetoxyphenyl)-2[(4-ethyl-2,3-dioxopiperazin-1-yl)carbonylamino]acetamido]-7α-formamido-3[(1-methyl-1H-tetrazol-5-yl)thiomethyl]-1-oxadethiaceph-3-em-4-carboxylic acid;

7β-[2-([4-ethyl-2,3-dioxopiperazin-1-yl]-carbonylamino)-2-phenylacetamido]-7α-formamido-3[(-methyl-1H-tetrazol-5-yl)-thiomethyl]-1-oxadethiaceph-3-em-4-carboxylic acid;

7β-[D-2-[(4-ethyl-2,3-dioxopiperazin-1-yl)carbonylamino]-2(3,4-dihydroxyphenyl)acetamido]-7α-formamido-3-[(1-methyl-1H-tetrazol-5-yl)thiomethyl]-1-oxadethiaceph-3-em-4-carboxylic acid;

7β-[D-2-(3,4-diacetoxyphenyl)-2[(4-ethyl-2,3-dioxopiperazin-1-yl)carbonylamino]acetamido]-7α-formamido-3-[(1-methyl-1H-tetrazol-5-yl)thiomethyl]-1-oxadethia-ceph-3-em-4-carboxylic acid; and b     7β-[D-2-[(4-ethyl-2,3-dioxopiperazin-1-yl]-carbonylamino)-2-phenylacetamido]-7α-formamido-3[(1-methyl-1H-tetrazol-5-yl)-thiomethyl]-1-oxadethia-ceph-3-em-4-carboxylic acid.

The antibiotic compounds according to the invention may be formulated for administration in any convenient way for use in human or veterinary medicine, according to techniques and procedures per se known in the art with reference to other antibiotics, and the invention therefore includes within its scope a pharmaceutical composition comprising an antibiotic compound according to the present invention such as, for example a compound of formula (I) above together with a pharmaceutically acceptable carrier or excipient.

The compositions may be formulated for administration by any suitable route, such as oral or parenteral, or by topical application. The compositions may be in the form of tablets, capsules, powders, granules, lozenges, creams or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxyethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository base, e.g. cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The composition may contain from 0.1% by weight, preferably from 1-60% by weight, of the active material, depending on the method of administration. Where the compositions comprise dosage units, each unit will preferably contain from 50-500 mg of the active ingredient. The dosage as employed for adult human treatment will preferably range from 100 to 10000 mg per day, for instance 1500 mg per day depending on the route and frequency of administration. Such a dosage corresponds to 1.5 to 50 mg/kg per day.

The antibiotic compound according to the present invention may be the sole therapeutic agent in the compositions of the invention or a combination with other antibiotics and/or β-lactamase inhibitor may be employed.

Advantageously the compositions also comprise a compound of formula (III) or a pharmaceutically acceptable salt or ester thereof:

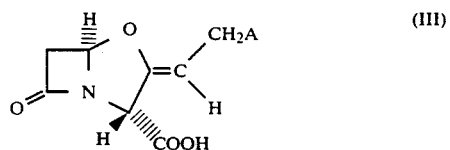

(III)

wherein A is hydroxyl, substituted hydroxyl, thiol, substituted thiol, amino, mono- or di-hydrocarbyl substituted amino, or mono- or di-acylamino.

A further advantageous composition comprises an antibiotic compound according to the invention together with a β-lactamase inhibitor of formula (IV) or a pharmaceutically acceptable salt or in vivo hydrolysable ester thereof:

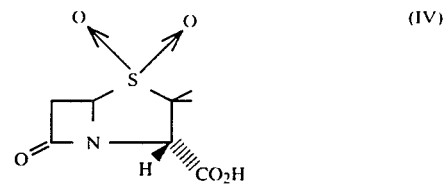

(IV)

Further suitable β-lactamase inhibitors include 6β-bromopenicillanic acid and salts and in vivo hydrolysable esters and 6β-iodopenicillanic acid and salts and in vivo hydrolysable esters thereof.

Such compositions of this invention comprising a β-lactamase inhibitor are formulated in conventional manner.

The present invention also includes a method of treating bacterial infections in humans and animals which comprises the administration of a therapeutically effective amount of an antibiotic compound of this invention.

The antibiotic compounds of the present invention are active against a broad range of gram positive and gram negative bacteria, in articular they are useful for treatment of respiratory tract and urinary tract infections in humans and mastitis in cattle. A particular advantage of the antibacterially active compounds of this invention is their stability to β-lactamase enzymes and they are therefore effective against β-lactamase producing organisms.

The present invention further provides a process for the preparation of a compound of formula (I) which process comprises formylating a compound of formula (V):

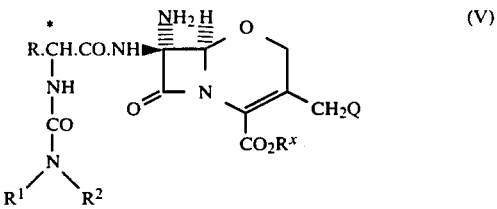

(V)

wherein R and Q are as hereinbefore defined and where any reactive groups may be protected; and $R^x$ is readily removable carboxy protecting group; and thereafter, if necessary, carrying out one or more of the following steps:

(i) removing any carboxy protecting groups
(ii) removing any protecting groups on R or Q
(iii) converting one group Q into a different group Q;
(iv) converting the product into a salt or in vivo hydrolysable ester thereof.

Suitable formylating agents include mixed anhydrides such as formic acetic anhydride. The reaction may suitably be carried out in a temperature in the range −50° C. to 30° C. in aprotic solvent such as, for example, dichloromethane, chloroform, dimethylformamide, tetrahydrofuran, hexamethylphosphoramide, or dimethylsulphoxide, in the presence of a tertiary base. A preferred tertiary base employed in the reaction is a base of the pyridine type, such as pyridine, lutidine or picoline.

Suitable readily removable carboxyl protecting groups for the group $-CO_2R^x$ in formula (I) include ester derivatives of the carboxylic acid. The derivative is preferably one which may readily be cleaved.

Suitable ester-forming carboxyl-protecting groups are those which may be removed under conventional conditions. Such groups for $R^x$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl, stannyl or phosphorus-containing group, an oxime radical of formula —N=CHR< where R< is aryl or heterocyclic, or an in vivo hydrolysable ester radical such as defined above.

The carboxyl group may be regenerated from any of the above esters by usual methods appropriate to the particular $R^x$ group, for example, acid—and base—catalysed hydrolysis, or by enzymically-catalysed hydrolysis, or by hydrogenolysis.

Compounds of the formula (V) may be prepared by the reaction of a corresposnding compound of the formula (VI):

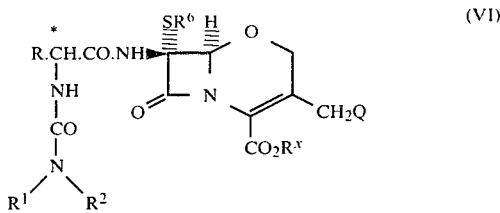

wherein Q, R and R and $R^x$ are as hereinbefore defined, and $R^6$ is $C_{1-6}$ alkyl, aryl, or benzyl: with anhydrous ammonia, an ammonium salt or an amine of the formula (VIA):

$$R^7—NH_2 \qquad (VIA)$$

wherein $R^7$ is a removable protecting group such as benzyl; in the presence of a metal ion such as mercury, silver, thallium, lead or copper and thereafter if necessary removing any protecting group to form the compound of formula (V).

Suitable examples of the alkyl group for $R^6$ include $C_{1-6}$ alkyl groups such as methyl, ethyl, n-, or iso propyl, and n-, sec-; iso-, or tert-butyl groups.

A preferred alkyl group for $R^6$ is methyl.

Suitable examples of the aryl group $R^6$ include phenyl, optionally substituted with $C_{1-6}$ alkyl, $C_{1-6}$ alkoxy, halogen, or nitro. Preferred aryl groups for $R^{19}$ include phenyl, o-, m- or p-methylphenyl, or o-, m- or p-nitrophenyl, in particular p-methylphenyl.

The preferred metal ion for use in the above process is the mercuric ion, aptly in the form of mercuric acetate.

Suitable solvents in which the reaction may be performed include for example, diethylether, tetrahydrofuran, dimethylformamide, methanol and hexamethylphosphoramide. The reactions are generally carried out under an inert atmosphere and at moderate to low temperatures i.e. in the range −100° C. to 30° C. The course of the reaction may be followed by conventional methods such as thin layer chromatography and terminated when an optimum quantity of product is present in the reaction mixture.

It will be appreciated that the processes for preparation of a compound of formula (V) described hereinbefore proceed via an imine intermediate; other processes proceding via such an intermediate are also included herein.

Compounds of the formula (VI) may be prepared by methods known or analogous to those known for the preparation of 7α-substituted-thio cephalosporins.

The compounds of formula (I) may also suitably be prepared by reacting a compound of formula (VII):

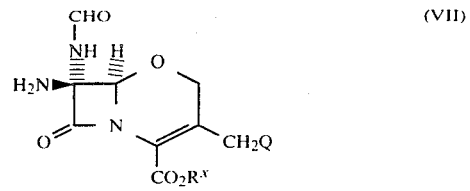

wherein the amino group is optionally substituted with a group which permits acylation to take place and $R^x$ and Q are as hereinbefore defined with reference to formula (V) above, with an N-acylating derivative of an acid of formula (VIII):

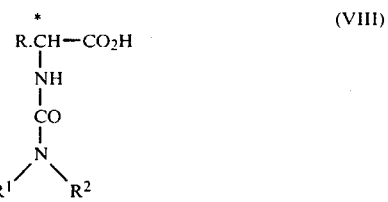

wherein R, $R^1$ and $R^2$ are as defined with respect to formula (I) and wherein any reactive groups therein may be protected; and thereafter, if necessary, carrying out one or more of the following steps:

(i) removing any carboxy-protecting group $R^x$;
(ii) removing any protecting groups on R and Q;
(iii) converting one group Q to a different group Q;
(iv) converting the product into a salt or in vivo hyrolysable ester thereof.

Suitable groups which permit acylation to take place and which are optionally present on the amino group of the starting material of the formula (VII) include N-silyl, N-stannyl and N-phosphorus groups, for example trialkylsilyl groups such as trimethylsily, trialkyltin groups such as tri-n-butyltin, groups of formula —P.-$R^aR^b$ wherein $R^a$ is an alkyl, haloalkyl, aryl, aralkyl, alkoxy, haloalkyl, aryl, aralkyl, alkoxy, haloalkoxy, aryloxy, aralkyloxy, or dialkylamino group, $R^b$ is the same as Ra or is halogen or $R^a$ and $R^b$ together form a ring; suitable such phosphorus groups being —P-$(OC_2H_5)_2$, —$P(C_2H_5)_2$,

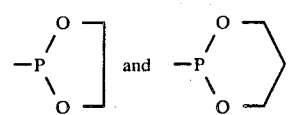

The carboxyl group may be regenerated from any of the above esters by usual methods appropriate to the particular $R^2$ group, for example, acid—and base—catalysed hydrolysis, or by enzymically—catalysed hydrogenolysis, or by hydrogenolysis.

Suitable carboxyl-protecting dericatives for the group —$CO_2R^x$ in formula (VII) are as described hereinbefore with reference to formula (V).

A reactive N-acylating derivative of the acid (VIII) is employed in the above process. The choice of reactive derivative will of course be influenced by the chemical nature of the substituents of the acid.

Suitable N-acylating derivatives include an acid halid, preferably the acid chloride or bromide. Acylation with an acid halide may be affected in the presence of an acid binding agent for example, tertiary amine (such as triethylamine, pyridine or dimethylaniline), an inorganic base (such as calcium carbonate or sodium bicarbonate) or an oxirane, which binds hydrogen halide liberated in the acylation reaction; The oxirane is preferably a $(C_{1-6})$-1,2-alkylene oxide—such as ehtylene oxide or propylene oxide. The acylation reaction using an acid halide may be carried out at a temperature in the range $-50°$ C. to $+50°$ C., preferably $-20°$ C. to $+20°$ C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl, isobutyl ketone or butyl acetate.

The acid halide may be prepared by reacting the acid (VIII) or a salt thereof with a halogenating (e.g. chlorinating or brominating) agent such as phosphorus pentachloride, thionyl chloride or oxalyl chloride.

Alternatively, the N-acylating derivative of the acid (VIII) may be a symmetrical or mixed anhydride. Suitable mixed anhydrides are alkoxyformic anhydrides, or anhydrides with, for example carbonic acid monoesters, trimethyl acetic acid, thioacetic acid, diphenylacetic acid, benzoic acid, phosphorus acids (such as phosphoric or phosphorous acids) or aliphatic or aromatic sulphonic acids (such as p-toluenesulphonic acid). When a symmetrical anhydride is employed, the reaction may be carried out in the presence of 2,6-lutidine as catalyst.

Alternatively N-acylating derivatives of acid (VIII) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimide, or 8-hydroxyquinoline; or amides such as N-acylsaccharins, N-acylthiazolidin-2-thione or N-acylphthalimides; or an alkylidene iminoester prepared by reaction of the acid (VIII) with an oxime.

Other reactive N-acylating lderivatives of the acid (VIII) include the reactive intermediates formed by reaction in situ with a condensing agent such as a carbodiimide, for example, N,N'-diethyl-, dipropyl- or diisopropylcarbodiimide, N,N'-di-cyclohexylcarbodiimide, or N-ethyl-N'-[3-(dimethylamino)propyl]carbodiimide; a suitable carbonyl compound, for example N,N'-carbonyldiimidazole or N,N'-carbonylditriazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3 —C_6H_6$); or a phosphoric acid condensing agent such as diethylphosphorylcyanide. The condensation reaction is preferably carried out in an organic reaction medium, for example methylene chloride, dimethylformamide, acetonitrile, alcohol, benzene, dioxan or tetrahydrofuran.

The compounds of formula (I) may also suitably be prepared by reacting a compound of formula (IX):

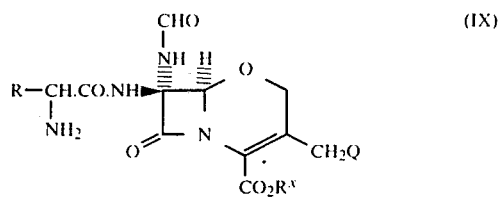
(IX)

wherein R, $R^x$ and Q are as hereinbefore defined and the α-amino group is optionally substituted with a group which permits acylation to take place and any reactive groups may be protected, with an N-acylating derivative of an acid of formula (X):

(X)

wherein $R^1$ and $R^2$ are as hereinbefore defined and wherein any reactive groups may be protected; and thereafter, if necessary, carrying out one or more of the following steps:

(i) removing any carboxyl-protecting group $R^x$;
(ii) removing any protecting groups on R or Q;
(iii) converting one group Q to a different group Q;
(iv) converting the product into a salt or in vivo hydrolysable ester thereof.

The compounds of formula (IX) herein which are intermediates for the compounds of formula (I) as hereinbefore defined may be prepared by reacting a compound of formula (VII) with an N-acylating derivative of an acid of formula (XI):

(XI)

wherein $R^{17}$ is an amino-protecting group and thereafter removing protecting group $R^{17}$.

Suitable amino protecting groups $R^{17}$ include those known in the art, with alkoxycarbonyl groups such as, for example, 4-nitrobenzyloxycarbonyl and trichloroethyloxycarbonyl being particularly preferred. The subgroup of compounds within the present invention of formula (XII):

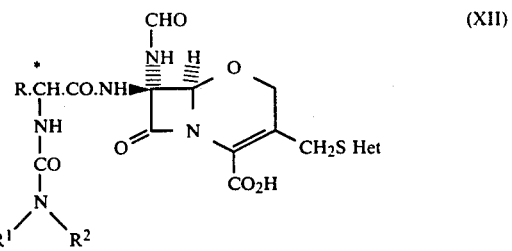
(XII)

wherein R and 'Het' are as defined hereinbefore with reference to formula (I), may suitably be prepared by reacting a compound of formula (XIII):

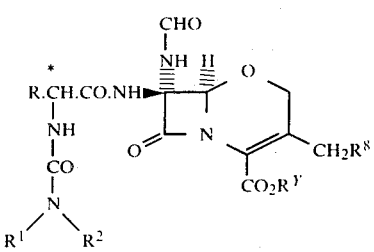

(XIII)

wherein R is as defined hereinbefore and wherein any reactive groups may be protected, $R^8$ is a leaving group and Ry is hydrogen or a group $R^x$ with a thiol of formula;

HetSH with the proviso that when $R^8$ is an acyloxy group $-CO_2R^y$ must be in the free acid form or a salt thereof and thereafter where necessary carrying out one or more of the following steps:

(i) removing any carboxyl—protecting group $R^x$;
(ii) removing any protecting groups on R; and
(iii) converting the product into a salt or in vivo hydrolysable after thereof.

Suitable leaving groups $R^8$ include halogen such as iodide or bromide or an acyloxy groups such as, for example the acetyloxy group.

The thiol HetSH may be reacted as the free compound or a salt with an alkali metal such as sodium or potassium. This reaction is desirably conducted in a solvent. For example, use can be made of water, or organic solvents inert to the starting compounds, such as dimethylformamide, dimethylacetamide, dioxane, acetone, alcohol, 1,2-dichloroethane, acetonitrile, dimethylsulfoxide or tetrahydrofuran, or mixtures thereof. The reaction temperature and time depend, among other factors, upon the starting compounds and solvent to be employed but generally the reaction is carried out at a selected temperature within the range of 0° to 100° C. for a selected time of a few hours to several days. The reaction is desirably conducted between pH 3 and 7.

To prevent oxidation of the thio compounds it is advantageous to carry out the reaction in an inert gaseous atmosphere, e.g. nitrogen gas. The subgroup of compounds within the present invention of formula (XIV):

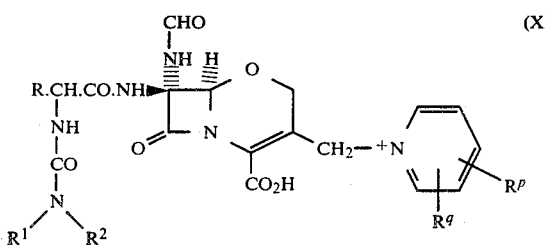

(XIV)

wherein R is as hereinbefore defined and $R^p$ and $R^q$ may be the same or different and each represents hydrogen, $C_{1-6}$ alkyl, $C_{1-6}$ alkyl, hydroxyalkyl, $C_{1-6}$ alkenyl, alkoxyalkyl, carboxyalkyl, sulphonylalkyl, carbamoylalkyl, carbamoyl, trifuoromethyl, hydroxy, halogen, and aminoalkyl may suitably be prepared by reacting a compound of formula (XIII) as hereinbefore defined with the appropriately substituted pyridine; and thereafter where necesary carrying out one or more of the following steps:

(i) removing any carboxyl—protecting group $R^x$;
(ii) removing any protecting groups on R; and
(iii) converting the product into a salt or in vivo hydrolysable ester thereof.

Suitably the reaction with the pyridine is carried out in a polar solvent such as water, and in the presence of a catalyst such as an alkali metal thiocyanate or an alkali metal halide such as, for example sodium iodide.

The antibiotic compounds of the present invention are active against a wide range of gram negative and gram positive organisms including *E.coli* such as, for example ESS, JT4, JT425 and NCTC 10418; *Pseudomonas Spp.* such as *Ps.aeruginosa* for example 10662 and Dalgleish; *Serratia marcescens* US32; *Klebsiella aerogenes* A; *Enterobacter cloacae* N1; *P.mirabilis* such as, for example C977 and 889; *P.morganii; P.rettgeri; B.subtilis; Staph aureus* such as, for example Oxford and Russel; *N.catarrhalis* 1502; *Strep faecalis* I; β-Haemolytic Strep CN10.

The following Examples illustrate the preparation and use of the compounds of the present invention.

EXAMPLE 1

Sodium 7β-[D-2-[4-ethyl-2,3-dioxopiperazin-1-yl-carbonylamino]-2-phenylacetamido]-7α-formamido-3-[(1-methyl-1H-tetrazol-5-yl)thiomethyl]-1-oxadethiaceph-3-em-4-carboxylate (a) Diphenylmethyl 3-[(1-methyl-1H-tetrazol-5-yl)thiomethyl]-7α-(4-nitrobenzylideneamino)-1-oxadethiaceph-3-em-4-carboxylate A solution of diphenylmethyl 7α-amino-3-[(1-methyl-1H-tetrazol-5-yl)thiomethyl]-1-oxadethia-ceph-3-em-4-carboxylate (U.K. Patent 1 592 245) (956 mg; 2.0 mmol) and 4-nitrobenzaldehyde (302 mg, 2.0 mmol) in an anhydrous mixture of toluene and ethyl acetate is stirred at room temperature over 4A molecular sieves. The reaction mixture is then filtered and the filtrate evaporated to dryness. The residue is re-evaporated from toluene (x2), and triturated with ether to give the title compound.

(b) Diphenylmethyl 3-[(1-methyl-1H-tetrazol-5-yl)thiomethyl]-7α-methylthio-7β-[4-nitrobenzylideneamino]-1-oxadethia-ceph-3-em-4-carboxylate Diphenylmethyl 3-[(1-methyl-1H-tetrazol-5-yl)thiomethyl]-7α-[4-nitrobenzylideneamino]-1-oxadethia-ceph-3-em-4-carboxylate (1.0 g; 1.6 mmol) is dissolved in anhydrous methylene dichloride (25 ml) containing methyl methanethiolsulphonate (225 mg; 1.8 mmol) and cooled to 0° C. under argon. To the vigorously stirred solution is added dropwise 1,8-diazabicyclo [5.4.0]undec-7-ene (248 mg; 1.6 mmol) in methylene dichloride (3 ml). The reaction is stirred at 0°-5° C., diluted with methylene dichloride and washed successively with saturated aqueous ammonium chloride (x2), brine, dried (MgSO₄) and evaporated. Chromatography of the residue afforded the title compound.

(c) Diphenylmethyl 7β-amino-3-[(1-methyl-1H-tetrazol-5-yl)thiomethyl]-7α-methylthio-1-oxadethia-ceph-3-em-4-carboxylate, toluene-p-sulphonic acid salt Diphenylmethyl-3-[(1-methyl-1H-tetrazol-5-yl)thiomethyl]-7α-methylthio-7β-(4-nitrobenzylideneamino)-1-oxadethia-ceph-3-em-4-carboxylate (657 mg; 1.0 mmol) is dissolved in a mixture of ethyl acetate and methylene dichloride and a solution of toluene-p-sulphonic acid monohydrate (190 mg; 1.0 mmol) in a little ethyl acetate added. Precipitation occurs almost immediately and when complete, the product is filtered off, washed well with ethyl acetate, ether and dried in vacuo to afford the title compound.

(d) Diphenylmethyl 7β-]D-2](4-ethyl-2,3-dioxopiperazin-1-yl)-carbonylamino]-2-phenylacetamido]-3-[(1-methyl-1H-tetrazol-5-yl)thiomethyl]7α-methylthio-1-oxadethia-ceph-3-em-4-carboxylate D-2-[(4-Ethyl-2,3-dioxopiperazin-1-yl)carbonylamino]-2-phenylacetic acid (479 mg; 1.5 mmol) in anhydrous methylene dichloride (15 ml) containing a catalytic amount of dimethylformamide, is treated with oxalyl chloride (419 mg; 3.3 mmol). After stirring at room temperature for 1.5 h the solution is evaporated to dryness, the residue redissolved in methylene dichloride and the solution evaporated; this is repeated. The resulting acid chloride is taken up in dry methylene dichloride and added dropwise with stirring to a mixture of diphenylmethyl 7-β-amino-3-[(1-methyl-1H-tetrazol-5-yl)-thiomeehyl]-7α-methylthio-1-oxadethia-ceph-3-em-4-carboxylate, toluene-p-sulphonic acid salt (695 mg; 1.0 mmol), and pyridine (180 mg; 2.2 mmol) in methylene dichloride (20 ml) ml) at 0° C. After stirring at 0° C. to room temperature, the reaction mixture is washed with dilute hydrochloric acid, saturated aqueous sodium hydrogencarbonate, brine, dried (MgSO4), and evaporated. Chromatography of the residue on silica gel gives the title compound.

(e) Diphenylmethyl 7α-amino-7β-[D-2-[(4-ethyl-2,3-dioxopiperazin-1-yl)-carbonylamino]-2-phenylacetamido]-3-[(1-methyl-1H-tetrazol-5-yl)thiomethyl]-1-oxadethiaceph-3-em-4-carboxylate Diphenylmethyl 7β-[D-2[(4-ethyl-2,3-dioxopiperazin-1-yl)-carbonylamino]-2-phenylacetamido]-3-[(1-methyl-1H-tetrazol-5-yl)thiomethyl]-7β-methylthio-1-oxadethia -ceph-3-em-4-carboxylate (246 mg; 0.3 mmol) in dry dimethylformamide (4 ml) at −50° C. under argon, is treated with mercuric acetate (104 mg; 0.3 mmol) in dimethylformamide, followed immediately by ammonia (5 mg; 0.3 mmol) in dimethylformamide (0.3 ml). The reaction mixture is stirred at −50° C. to −20° C., poured into ethyl acetate and washed well with water and brine. The organic solution is dried over magnesium sulphate, evaporated, and the residue chromatographed on silica gel to afford the title product.

(f) Diphenylmethyl 7β-[D-2-[(4-ethyl-2,3-dioxopiperazin-1-yl)carbonylamino]-2-phenylacetamido]-7α-formamido-3-[(1-methyl-1H-tetrazol-5-yl)thiomethyl]-1-oxadethia-ceph-3-em-4-carboxylate A solution of diphenylmethyl 7α-amino-7β-[D-2[(4-ethyl-2,3-dioxopiperazin-1-yl)-carbonylamino]-2phenylacetamido]-3-[(1-methyl-1H-tetrazol-5-yl)thiomethyl]-1-oxadethia-ceph-3-em-4-carboxylate (200 mg; 0.25 mmol) and pyridine (200 mg; 2.5 mmol) in methylene dichloride (8 ml) is cooled to 0° C. and treated with acetic-formic anhydride (111 mg; 1.25 mmol). The reaction is stirred at 0° C.–10° C. and then diluted with dry toluene and evaporated. The residue is redissolved in dry toluene and the solution is evaporated; this is repeated twice. Chromatography of the residue on silica gel gives the title compound.

(g) Alternative route to Diphenylmethyl-7β-[D-2-[(4-ethyl-2,3-dioxopiperazin-1-yl)-carbonylamino]-2-phenylacetamido]-7α-formamido-3[(1-methyl-1H-tetrazol-5-yl)-thiomethyl]-1-oxadethia-ceph-3-em-4-carboxylate Diphenylmethyl 7β-[D-2-[(4-ethyl-2,3-dioxopiperazin-1-yl)-carbonylamino[-2-phenylacetamido]-3-[(1-methyl-1H-tetrazol-5-yl)thiomethyl]-7α-methylthio-1-oxadethia-ce ph-3-em-4-carboxylate (205 mg; 0.25 mmol) in dimethylformamide (5 ml), is treated successively with bis-trimethylsilylformamide (102 mg; 0.5 mmol) and mercuric acetate (87 mg; 0.28 mmo!) in dimethylformamide (1 ml). The reaction mixture is partitioned between ethylacetate and water, and the organic layer separated. The latter is washed successively with water, dilute aqueous sodium hydrogen carbonate, and brine, dried and evaporated. Chromatography on silica affords the title compound.

(h) Sodium 7β-[D-2-[(4-ethyl-2,3-dioxopiperazin-1-yl)-carbonylamino]-2-phenylacetamido]-7α-formamido-3-[(1-methyl-1H-tetrazol-5-yl)thiomethy]-1-oxadethia-ceph-3-em-4-carboxylate Diphenylmethyl 7βD-2-[(4-ethyl-2,3-dioxopiperazin1-yl)carbonylamino]-2-phenylacetamido]-7α-formamido-3[(1-methyl-1H-tetrazol-5-yl)thiomethyl]-1-oxadethiaceph-3-em-4-carboxylate (50 mg; 0.06 mmol) is dissolved in ice-cold anhydrous methylene dichloride (1 ml) containing anisole (0.1 ml), and trifluoroacetic acid (0.1 ml) added. The mixture is stirred at 0° C. and is then evaporated. The residue is redissolved in dry toluene and the solution evaporated; this is repeated twice. The residue is dissolved in dilute aqueous sodium hydrogen carbonate solution and passed through a Diaion HP20 SS column. The product containing fractions are lyophilised to give the title compound as a solid.

EXAMPLE 2

Sodium 7β-[2-(3,4-diacetoxyphenyl)-2-[(4-ethyl-2,3-dioxopiperazin-1-yl)-carbonylamino]acetamido]-7α-formamido-3[(1-methyl-1H-tetrazol-5-yl)thiomethyl]-1-oxadethia-ceph-3-em-4-carboxylate (a) Diphenylmethyl 7β-[2-(3,4-diacetoxyphenyl)-2[(4-ethyl-2,3-dioxopiperazin-1-yl)-carbonylamino]acetamido]-3-[(1-methyl-1H-tetrazol-5-yl)thiomethyl]-7α-methylthio-1-oxadethiaceph-3-em-4-carboxylate Diphenylmethyl 7β-amino-3-[(1-methyl-1H-tetrazol-5-yl)thiomethyl]-7α-methylthio-1-oxadethia-ceph-3-em-4-carboxylate prepared either as described in Example 1 or as described by Y. Sendo and M. Yoshioka J.C.S.Chem.Comm. 1980, 1069 (261 mg; 0.5 mmol) in methylene dichloride (10 ml) with N,N¹-dicyclohexylcarbodiimide (87 mg; 0.42 mmol) is treated slowly with a solution of 2-(3,4-diacetoxyphenyl)-2-[(4-ethyl-2,3-dioxopiperazin-1-yl)carbonylamino]acetic acid (175 mg; 0.4 mmol) in methylene dichloride. The reaction is stirred at room temperature, and on completion (t.l.c. monitor) is filtered and evaporated. The residue is chromatographed on silica gel to afford the title compound.

(b) Diphenylmethyl 7β-[2-(3,4-diacetoxyphenyl) -2-[(4-ethyl-2,3-dioxopiperazin-1-yl)carbonylamino]acetamido]-7α-formamido-3-[(1-methyl-1H-tetrazol-5-yl)thiomethyl]-1-oxadethia-ceph-3-em-4-carboxylate Diphenylmethyl 7β[2-(3,4-diacetoxyphenyl)-2-[(4-ethyl-2,3-dioxopiperazin-1-yl)carbonylamino]acetamido]-3-[(1-methyl-1H-tetrazol-5-yl)thiomethyl]-7α-methylthio-1-oxadethia-ceph-3-em-4-carboxylate (100 mg; 0.11 mmol) is converted to the title compound using either the procedure described in Example 1 (e)/1(f) or Example 1(g).

(c) Sodium 7β-[2-(3,4-diacetoxyphenyl)-2-[(4-ethyl-2,3-dioxopiperazin-1-yl)-carbonylamino]acetamido]-7α-formamido-3[(1-methyl-1H-tetrazol-5-yl) thiomethyl]-1-oxadethia-ceph-3-em-4-carboxylate Diphenylmethyl 7β-[2-(3,4-diacetoxyphenyl)-2 [4-ethyl-2,3-dioxopiperazin-1-yl)carbonylamino]acetamido]-7α-formamido-3[(1-methyl-1H-tetrazol-5-yl) thiomethyl]-1-oxadethia-ceph-3-em-4-carboxylate (30 mg; 0.03 mmol) is dissolved in anhydrous methylene dichloride (0.5 ml), cooled to 0° C. and vigorously stirred while anisole (0.04 ml) and trifluoroacetic acid (0.05 ml) are added. After stirring at 0° C., the solution is evaporated and the residue taken up in toluene and re-evaporated to dryness; this process is repeated. The residue is triturated with ether, taken up in water which is adjusted to pH 6.5 with saturated sodium hydrogencarbonate solution, washed with ethyl acetate and lyophilised to give the title compound.

EXAMPLE 3

Sodium 7β-[2-[(4-ethyl-2,3-dioxopiperazin-1-yl) carbonylamino]-2-(3,4-dihydroxyphenyl)acetamido]-7α-formamido-3-[(1-methyl-1H-tetrazol-5-yl)thiomethyl]-1-oxadethia-ceph-3-em-4-carboxylate Sodium 7β-[2-(3,4-diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-1-oxadethia-ceph-3-em-4-carboxylate (75 mg) is stirred in dilute sodium hydrogencarbonate solution at pH 8.5. The cooled reaction mixture is then carefully acidified, saturated with sodium chloride and repeatedly extracted with tetrahydrofuran-ethyl acetate mixtures. The combined extracts are washed with brine, dried, and evaporated. The residue, in tetrahydrofuran-ethylacetate, is treated with 2N sodium ethyl hexanoate in 4-methylpentan-2-one and diluted with ether. The precipitate is filtered, washed with tetrahydrofuran, ether and dried to give the title compound.

EXAMPLE 4

Sodium 7β-[D-2-([4-Ethyl-2,3-dioxopiperazin-1-yl]carbonylamino)-2-phenylacetamido]-7α-formamido-3[(1-methyl-1H-tetrazol-5-yl)-thiomethyl]-1-oxadethia-ceph-3-em-4-carboxylate (a) Diphenylmethyl 3-[(1-methyl-1H-tetrazol-5-yl)thiomethyl]-7α-(4-nitrobenzylideneamino)-1-oxadethia-ceph-3-em-4-carboxylate A solution of diphenylmethyl 7α-amino-3-[(1-methyl-1H-tetrazol-5-yl)-thiomethyl]-1-oxadethia-ceph-3-em-4-carboxylate (U.K. Patent No. 1 592 245) (1.305 g; 2.7 mmol) and 4-nitrobenzaldehyde (0.389 g; 2.6 mmol) in an anhydrous mixture of toluene (35 ml) and dichloromethane (7 ml) was stirred at room temperature over 4A molecular sieves for 24 h. The reaction mixture was then filtered and the filtrate evaporated to dryness. The residue is re-evaporated from toluene (x2), and triturated with ether to give the title compound (1.24 g; 75%). $\nu_{max}$ (Nujol) 1780, 1718, 1630 cm$^{-1}$; δppm (CDCl$_3$) 3.86 (3H, s), 4.32 (2H, s), 4.65 and 4.78 (2H, ABq, J 18 Hz), 4.81 (1H, s), 5.22 (1H, s), 6.97 (1H, s), 7.2–7.6 (10H, m), 7.95 (2H, d, J 8.8 Hz), 8.30 (2H, d, J 8.8 Hz), 8.57 (1H, d, J 1 Hz).

(b) Diphenylmethyl 3-[(1-methyl-1H-tetrazol-5-yl)thiomethyl]-7α-methylthio-7β-[4-nitrobenzylideneamino]-1-oxadethia-ceph-3-em-4-carboxylate Diphenylmethyl 3-[(1-methyl-1H-tetrazol-5-yl)thiomethyl]-7α-(4-nitrobenzylideneamino)-1-oxadethia-ceph-3-em-4-carboxylate (151 mg; 0.247 mmol) was dissolved in dry N,N-dimethylformamide (2 ml), containing methyl methanethiolsulphonate (60 mg; 0.494 mmol), cooled to −20° C. under argon and powdered anhydrous potassium carbonate (38 mg; 0.271 mmol) added. The reaction mixture was vingorously stirred at −20° C.−−15° C. for 2.25 h., and then poured into ethyl acetate and water. The aqueous phase was separated and extracted with ethyl acetate. The combined organic fractions were washed with water, brine, dried (MgSO$_4$) and evaporated to an oil. Chromatography of the residue gave the title compound (82 mg; 51%). $\nu_{max}$ (CHCl$_3$) 1780, 1715, 1630, 1520, 1350 cm$^{-1}$; δppm (CDCl$_3$) 2.31 (3H, s), 3.84 (3H, s), 4.30 (2H, AA$^1$), 4.64 and 4.78 (2H, ABq, J 19 Hz), 5.19 (1H, s), 6.92 (1H, s), 7.20–7.6 (10H, m), 8.03 (2H, d, J 8 Hz), 8.29 (2H, d, J 8 Hz), 8.89 (1H, s).

(c) Diphenylmethyl 7β-amino-3-[(1-methyl-1H-tetrazol-5-yl)thiomethyl]-7α-methylthio-1-oxadethia-ceph-3-em-4-carboxylate Diphenylmethyl-3-[(1-methyl-1H-tetrazol-5-yl) thiomethyl]-7α-methylthio-7β-(4-nitrobenzylideneamino)-1-oxadethia-ceph-3-em-4-carboxylate (471 mg; 0.72 mmol) was dissolved in ethyl acetate (2 ml) and a solution of toluene-p-sulphonic acid monohydrate (149 mg; 0.78 mmol) in a little ethyl acetate added. After stirring at room temperature for 1 hour, hexane was added to complete the precipitation of the product, which was filtered off, washed well with ethyl acetate, ether and dried in vacuo to give diphenylmethyl 7-β-amino-3-[(1-methyl-1H-tetrazol-5-yl)thiomethyl]-7α-methylthio-1-oxadethia-ceph-3-em-4-carboxylate, p-toluene sulphonic acid salt (431 mg; 93%). $\nu_{max}$(Nujol) 3400, 1795, 1720, 1620 cm$^{-1}$; δppm [(CD$_3$)$_2$SO] 2.28 (3H,s), 2.41 (3H,s), 3.4–3.6(3H, broad s), 3.89 (3H,s), 4.28(2H, AA$^1$), 4.72 and 4.87 (2H, ABq, J19 Hz), 5.44(1H,s), 6.88(1H,s), 7.1–7.7(14H,m). The salt was suspended in ethyl acetate, treated with dilute sodium hydrogencarbonate solution and the organic phase separated, washed with brine, dried and evaporated to give the title compound (253 mg; 80%). ν$_{max}$ (CHCl$_3$) 3375, 1785, 1720, 1625 cm$^{-1}$; δppm (CDCl$_3$) 2.09 (2H, broad s), 2.33 (3H,s), 3.85(3H,s), 4.30(2H,AA$^1$), 4.63 and 4.80 (2H,ABq, J18.8 Hz), 4.88(1H,s), 6.92(1H,s), 7.2–7.6 (10H,m).

(d) Diphenylmethyl 7β-[D,2-((4-Ethyl-2,3-dioxopiperazin-1-yl)carbonylamino)-2-phenyl acetamido]-3-[(1-methyl-1H-tetrazol-5-yl)thiomethyl]-7α-methylthio-1-oxadethia-ceph-3-em-4-carboxylate.

D-2-[(4-Ethyl-2,3-dioxopiperazin-1-yl)carbonylamino]-2-phenylacetic acid (122 mg; 0.38 mmol) in anhydrous dichloromethane (3 ml) containing a catalytic amount of dimethyl formamide, was treated with oxalyl chloride (106 mg; 0.83 mmol). After stirring at room temperature for 1 hour the solution was evaporated to dryness, the residue redissolved in dichloromethane and the solution evaporated; this was repeated. The resulting acid chloride was taken up in dichloromethane (2 ml) and added to diphenylmethyl 7-β-amino-3-[(1-methyl-1H-tetrazol-5-yl)-thiomethyl]-7α-methylthio-1-oxadethia-ceph-3-em-4-carboxylate (100 mg; 0.2 mmol) in dichloromethane (2 ml) at −10° C., followed by dropwise addition of pyridine (17 mg; 0.22 mol) in dichloromethane. After stirring at −10° C. to 0° C. for 0.5 hour, the reaction mixture was washed with dilute hydrochloric acid, saturated aqueous sodium hydrogencarbonate, brine, dried (MgSO$_4$), and evaporated. Chromatography of the residue on silica gel gave the title compound (124 mg; 79%). ν$_{max}$ (CHCl$_3$) 3400, 3275, 1790, 1715, 1690, 1630 cm$^{-1}$; δppm [(CD$_3$)$_2$CO] 1.18(3H,t,J7 Hz), 2.29(3H,s), 3.51 (2H,q,J 7 Hz), 3.70(2H,m), 3.95(3H,s), 4.06(2H,m), 4.29(2H,AA$^1$), 4.52 and 4.61 (2H,ABq, J16 Hz), 5.04(1H,s), 5.70(1H,d,J6 Hz), 7.89(1H,s), 7.2–7.7 (16H,m), 9.92(1H,d,J6 Hz).

(e) Diphenylmethyl 7α-amino-7β-[D-2-((4-ethyl-2,3-dioxopiperazin-1-yl)carbonylamino)-2-phenylacetamido]-3-[(1-methyl-1H-tetrazol-5-yl)thiomethyl]-1-oxadethia-ceph-3-em-4-carboxylate.

Method A

Diphenylmethyl 7β-[D-2((4-ethyl-2,3-dioxopiperazin-1-yl)carbonylamino)-2-phenylacetamido]-3-[(1-methyl-1H-tetrazol-5-yl)thiomethyl]-7α-methylthio-1-oxadethia-ceph-3-em-4-carboxylate (30 mg; 0.036 mmol) was dissolved in anhydrous dioxan (1 ml) at room temperature and peracetic acid (53 μl of a 5.2% w/v solution in acetic acid) added. After 0.5 hour, the solution was evaporated to dryness, redissolved in toluene and re-evaporated; this process was repeated. The residue was chromatographed to give diphenylmethyl 7β-[D-2((4-ethyl-2,3-dioxopiperazin-1-yl)carbonylamino)-2-phenylac etamido]-3-[(1-methyl-1H-tetrazol-5-yl)thiomethyl]-7α-m ethylsulphinyl-1-oxadethia-ceph-3-em-4-carboxylate (22 mg; 72%), ν$_{max}$ (CHCl$_3$) 3260, 1795, 1690, 1630, 1055 cm$^{-1}$ which was dissolved in anhydrous tetrahydrofuran (2 ml) at room temperature and reacted with ammonia (1.17 ml; 0.052 mmol). The solution was evaporated after 16 hour and chromatographed to give the title compound (11 mg; 37%) ν$_{max}$ (CHCl$_3$) 3380, 3275, 1790, 1715, 1690, 1630 cm$^{-1}$; δppm [(CD$_3$)$_2$CO] 1.16 (3H,t,J7 Hz), 3.50(2H,q,J7 Hz), 3.69 (2H,m), 3.94 (3H,s), 4.05 (2H,m), 4.25(2H,AA$^1$) and 4.55 (2H,ABq, J17 Hz) 4.93 (1H,s), 5.66(1H,d,J 7 Hz), 6.92(1H,s), 7.2–7.8 (16H,m), 9.95(1H,d,J 7 Hz), and diphenylmethyl 7β-amino-7α-[D,2-((4-ethyl-2,3-dioxopiperazin-1-yl)carbonylamino)-2-phenylacetamido]-3-[(1-methyl-1H-tetra zol-5-yl)thiomethyl]-1-oxadethia-ceph-3-em-4-carboxylate δppm [(CD$_3$)$_2$CO] inter alia 1.16 (3H,t,J7 Hz), 3.50 (2H,q,J7 Hz), 3.69 (2H,m), 3.95(3H,s), 4.05(2H,m), 4.30(2H,AA$^1$), 4.66 and 4.77(2H,ABq,J17 Hz), 5.02(1H,s), 5.66(1H,d,J 7 Hz), 6.93(1H,s), 7.2–7.8 (16H,m), 10.05(1H,d,J 7 Hz), as an inseparable mixture.

Method B

Diphenylmethyl 7β-[D,2-((4-ethyl-2,3-dioxopiperazin-1-yl)carbonylamino)-2-phenylacetamido]-3-[(1-methyl-1H-tetrazol-5-yl)thiomethyl]-7α-methylthio-1-oxadethiaceph-3-em-4-carboxylate (25 mg; 0.03 mmol) in dry dimethylformamide (0.5 ml) at −50° C. under argon was treated with ercuric acetate (9.6 mg; 0.03 mmol) in dimethylformamide, followed immediately by ammonia (0.52 mg; 0.03 mmol) in dimethylformamide (0.1 ml). The reaction mixture was stirred at −50° C. to −20° C., for 1 hour, poured into ethyl acetate and washed well with water and brine. The organic solution was dried over magnesium sulphate, evaporated, and the residue chromatographed to afford the title product as in Method A.

(f) Diphenylmethyl 7β-[D-2-((4-Ethyl-2,3-dioxopiperazin-1-yl)carbonylamino)-2-phenylacetamido]-7α-formamido-3-[(1-methyl-1H-tetrazol-5-yl)thiomethyl]-1-oxadethia-ceph-3-em-4-carboxylate.

Diphenylmethyl 7β-[D-2-((4-ethyl-2,3-dioxopiperazin-1-yl)carbonylamino)-2-phenylacetamido]-7α-amino-3-[(1-methyl-1H-tetrazol-5-yl)thiomethyl]-1-oxadethia-ceph-3-em-4-carboxylate (46 mg containing some 7β-amino isomer as described in (e); 0.057 mmol) in dry dichloromethane (2 ml) at 0° C. under argon was treated with pyridine (27 mg; 0.34 mmol) and formicacetic anhydride (15 mg, 0.17 mmol). After 0.75 hour at 0° C. and 1.25 hour warming to room temperature, the reaction mixture was diluted with toluene, and evaporated. The residue was treated with fresh toluene and evaporated; this process was repeated. Chromatography of the residue gave the title compound. ν$_{max}$ (CHCl$_3$) 3400sh, 3275, 1795, 1720, 1715, 1690, 1630sh cm$^{-1}$; δppm [(CD$_3$)$_2$CO] 1.16 (3H,t,J 7 Hz), 3.50(2H,q,J7 Hz), 3.70 (2H,m), 3.95(3H,s), 4.05(2H,m), 4.2 and 4.32 (2H,ABq, J 13 Hz), 4.39 and 4.55 (2H, ABq, J 19 Hz), 5.25(1H,s), 5.70 (1H,d,J 6 Hz), 6.90 (1H,s), 7.2–7.8 (15H,m), 8.27(1H,s) 9.95 (1H,d,J 6 Hz) and diphenylmethyl 7α-[D,2((4-ethyl-2,3-dioxopiperazin-1-yl)carbonylamino)-2-phenylacetamido]-7β-formamido-3-[(1-methyl-1H-tetrazol-5-yl)thiomethyl]-1-oxadethia-ceph-3-em-4-carboxylate ν$_{max}$ (CHCl$_3$) 3400sh, 3275, 1795, 1720, 1715, 1690, 1630 cm$^{-1}$; δppm [(CD$_3$)$_2$CO] inter alia 1.16 (3H,t,J 7 Hz), 3.50 (2H,q,J 7 Hz), 3.70(2H,m), 3.92(3H,s), 4.05(2H,m), 4.32(2H,AA$^1$), 4.74(2H,AA$^1$), 5.18 (1H,s), 5.71(1H,d,J 6 Hz), 6.92(1H,s), 7.2–7.8 (15H,m), 8.16(1H,s), 9.96 (1H,d,J 6 Hz).

(g) Sodium 7β-[D,2-((4-Ethyl-2,3-dioxopiperazin-1-yl)carbonylamino)-2-phenylacetamido]-7α-formamido-3-[(1-methyl-1H-tetrazol-5-yl)thiomethyl]-1-oxadethiaceph-3-em-4-carboxylate Diphenylmethyl 7β-[D,2-((4-ethyl-2,3-dioxopiperazin-1-yl)-carbonylamino]-2-phenylacetamido]-7α-formamido-3[(1-methyl-1H-tetrazol-5-yl)thiomethyl-1-oxadethia-ceph-3-em-4-carboxylate (35 mg; containing some 7β-formamido isomer as described in (f); 0.04 mmol) was dissolved in anhydrous dichloromethane (1.5 ml) containing anisole (0.135 ml) at 0° C. and trifluoroacetic acid (0.16 ml) added. After 15 minutes, the pink solution was diluted with toluene and the solution evaporated. The residue was redissolved in toluene and evaporated to dryness; this was repeated. The residue was triturated with ether to give a white solid which was dissolved in water-sodium hydrogencarbonate to pH 6.5, and passed through Diaion HP20SS. The product containing fractions were lyophilised to give the title compound (17 mg; 59%). $\lambda_{max}$ (H$_2$O) 257 mm, Em (13066) $\nu_{max}$ (KBr) 3435, 3250, 1779, 1710, 1678, 1611 cm$^{-1}$; δppm (D$_2$O). inter alia 1.20 (3H,t,J 7 Hz) 3.51 (2H,q,J 7 Hz), 3.71(2H,m), 3.99(3H,s), 4.0(2H,m), 5.24(1H,s), 5.53(1H,s), 7.35–7.55(5H,m), 8.10(1H,s).

MIC against P Mirabilis 0.12 μg ml$^{-1}$.

EXAMPLE 5

Sodium 7β-[D-2-(3,4-diacetoxyphenyl)-2-([4-ethyl-2,3-dioxopiperazin-1-yl]-carbonylamino)acetamido]-7α-formamido-3[(1-methyl-1H-tetrazol-5-yl)thiomethyl]-1-oxadethia-ceph-3-em-4-carboxylate (a) Diphenylmethyl 7β-[D-2-(3,4-diacetoxyphenyl)-2-([4-ethyl-2,3-dioxopiperazin-1-yl]carbonylamino)acetamido]-3[(1-methyl-1H-tetrazol-5-yl)thiomethyl]-7α-methylthio-1-oxadethia-ceph-3-em-4-carboxylate D-2-(3,4-Diacetoxyphenyl)-2-[(4-ethyl-2,3-dioxopiperazin-1-yl)carbonylamino]acetic acid (165 mg; 0.41 mmol) in anhydrous dichloromethane (2 ml) containing a catalytic amount of dimethylformamide, was cooled to 0° C. and oxalyl chloride (106 mg; 0.83 mmol) added. After stirring at room temperature for 1 hour, the solution was evaporated to dryness, the residue redissolved in dichloromethane and the solution evaporated; this was repeated. The resulting acid chloride was taken up in dichloromethane (2 ml) and added to diphenylmethyl 7β-amino-3[(1-methyl-1H-tetrazol-5-yl)thiomethyl]-7α-methylthio-1-oxadethia-ceph-3-em-4-carboxylate (100 mg; 0.2 mmol) in dichloromethane (3 ml) at −10° C., followed by pyridine (17 mg; 0.22 mol) in dichloromethane (0.5 ml). After stirring at −10° C. to 0° C. for 1.25 hour, the reaction was diluted with ethyl acetate, washed with dilute hydrochloric acid, brine, dilute sodium hydrogencarbonate, brine, dried (MgSO$_4$) and evaporated. Chromatography of the residue on silica gel afforded the title product (107 mg; 62%). $\nu_{max}$ (CHCl$_3$) 3275, 1780, 1715, 1690, 1625(sh) cm$^{-1}$; δppm [(CD$_3$)$_2$CO] inter alia 1.16 (3H,t,J7 Hz), 2.20, 2.25, 2.29 and 2.31(together 6H,s), 2.26(3H,s), 3.51(2H,q,J7 Hz), 3.71(2H,m), 3.94 and 3.96 (3H,s), 4.05 (2H,m), 4.26 and 4.38 (ABq, J13 Hz) and 4.32(s), together 2H, 4.50 and 4.61 (ABq, J18 Hz), 5.01 and 5.06 (together 1H,s), 5.74 and 5.77 (together 1H,s), 6.90 and 6.92 (together 1H,s), 7.15–7.70(13H,m).

(b) Diphenylmethyl 7α-amino-7β-[D-2-(3,4-diacetoxyphenyl)-2-[(4-ethyl-2,3-dioxopiperazin-1-yl)carbonylamino]acetamido]-3-[(1-methyl-1H-tetrazol-5-yl)thiomethyl]-1-oxadethiaceph-3-em-4-carboxylate Diphenylmethyl 7β-[D-2-(3,4-diacetoxyphenyl)-2-[(4-ethyl-2,3-dioxopiperazin-1-yl)carbonylamino]acetamido]-7α-methylthio-3-[(1-methyl-1H-tetrazol-5-yl) thiomethyl]-1-oxadethiaceph-3-em-4-carboxylate (144 mg; 0.16 mmol) was dissolved in anhydrous dichloromethane (5 ml), cooled to −20° C. and peracetic acid (0.277 ml, of a 5.2% w/v solution in acetic acid) added. After 15 min the reaction mixture was diluted with toluene and evaporated; the residue was redissolved in dry toluene and re-evaporated; this process was repeated. The residue was chromatographed to give diphenylmethyl 7α-[D-2-(3,4-diacetoxyphenyl)-2-[(4-ethyl-2,3-dioxopiperazin-1-yl)carbonylamino]acetamido]-3-[(1-methyl-H-tetrazol-5-yl)thiomethyl]-7α-methylsulphinyl-1-oxadethia-ceph-3-em-4-carboxylate (140 mg; 98%), $\nu_{max}$ (CHCl$_3$) 3275, 1795, 1775, 1715, 1690, 1630(sh), 1060 cm$^{-1}$; which was dissolved in anhydrous tetrahydrofuran (10 ml) at room temperature and reacted with ammonia (7 ml; 0.31 mmol). The solution was evaporated after 16 hour and chromatographed to give the title compound (42 mg:30%). $\nu_{max}$ (CHCl$_3$) 3250 br, 1790,1780, 1715, 1690 cm$^{-1}$; δppm [(CD$_3$)$_2$CO] inter alia 1.16(3H,tJ 7 Hz), 2.27 (6H,s), 3.51 (2H,q,J7 Hz), 3.70 (2H,m), 3.94(3H,s), 4.05(2H,m), 4.22 and 4.32 (2H,ABq, J13 Hz), 4.44 and 4.56(2H,ABq, J19 Hz), 4.96(1H,s), 5.69(1H,s), 6.93(1H,s), 7.15–7.70(13H,m) and diphenylmethyl 7β-amino-7α-[D,2-(3,4-diacetoxyphenyl)-2-[(4-ethyl-2,3-dioxopiperazin- 1-yl)carbonylamino]acetamido]-3-[(1-methyl-1H-tetrazol-5-yl)thiomethyl]-1-oxadethia-ceph-3-em-4-carboxylate δppm [(CD$_3$)$_2$CO] inter alia 1.16 (3H,t,J7 Hz), 2.26(6H,s), 3.51(2H,q,J7 Hz), 3.70(2H,m), 3.96(3H,s), 4.05(2H,m), 4.29(2H,s), 4.62(2H,AA'), 4.94(1H,s), 5.71(1H,s), 6.94(1H,s), 7.17–7.70(13H,m), as an inseparable mixture.

(c) Diphenylmethyl 7β-[D,2-(3,4-diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-1-oxadethiaceph-3-em-4-carboxylate Diphenylmethyl 7β-[D,2-(3,4-diacetoxyphenyl)-2-[(4-ethyl-2,3-dioxopiperazin-1-yl)carbonylamino]acetamido]-7α-amino-3-[(1-methyl-1H-tetrazol-5-yl)thiomethyl]-1-oxadethia-ceph-3-em-4-carboxylate (42 mg; 0.05 mmol; containing some 7β-amino as described in (b)), in anhydrous dichloromethane (2 ml) at 0° C. under argon was treated with pyridine (23 mg; 0.3 mmol) and formic-acetic anhydride (12.6 mg; 0.15 mmol) as described in Example 4 (f) to give the title compound, $\nu_{max}$ (CHCl$_3$) 3275, 1790, 1775, 1710, 1690, 1620(sh) cm$^{-1}$, δppm [(CD$_3$)$_2$CO] inter alia 1.17(3H,t,J7 Hz), 2.26(6H,s), 3.51(2H,q,J7 Hz), 3.70(2H,m), 3.94(3H,s), 4.05(2H,m), 4.23 and 4.34(2H, ABq, J12 Hz), 4.41 and 4.55(2H,ABq, J18 Hz), 5.27(1H,s), 5.75(1H,s), 6.92(1H,s), 7.15–7.8 (13H,m), 8.28(1H,s) and diphenyl 7α-[D,2-(3,4-diacetoxyphenyl)-2-[(4-ethyl-2,3-dioxopiperazin-1-yl)carbonylamino]acetamido]-7β-formamido-3-[(1-methyl-1H-tetrazol-5-yl)thiomethyl]-1-oxadethia-ceph-3-em-4-carboxylate δ[(CD$_3$)$_2$CO] inter alia 1.17(3H,t,J7 Hz), 2.25(6H,s), 3.50(2H,q,J7 Hz), 3.70(2H,m), 3.95(3H,s), 4.05(2H,m), 4.33(2H,s), 5.77(1H,s), 6.94(1H,s), 7.15–7.80(13H,m), 8.22 (1H,s), (35 mg; 81%).

(d) Sodium 7β-[D,2-(3,4-diacetoxyphenyl)-2-[(4-ethyl-2,3-dioxopiperazin-1-yl)carbonylamino]acetamido]-7α-formamido-3-[(1-methyl-1H-tetrazol-5-yl)thiomethyl]-1-oxadethia-ceph-3-em-4-carboxylate Diphenylmethyl 7β-[D,2-(3,4-diacetoxyphenyl)-2-[(4-ethyl-2,3-dioxopiperazin-1-yl)carbonylamino]acetamido]-7α-formamido-3-[(1-methyl-1H-tetrazol-5-yl thiomethyl]-1-oxadethia-ceph-3-em-4-carboxylate (33 mg; 0.035 mmol) containing some 7β-formamido as described in (c)), was dissolved in anhydrous dichloromethane (1.2 ml) containing anisole (0.111 ml) at 0° C. and trifluoroacetic acid (0.132 ml) added. After 15 min the reaction mixture was worked up and purified as described in Example 4(g) to give the title compound (21 mg:78%). $\nu_{max}$ (H$_2$O) 528 mm, (Em 11988); $\nu_{max}$ (KBr) 3431, 1771, 1710, 1679, 1611 cm$^{-1}$; δppm (D$_2$O) inter alia 1.19(3H,t,J 7 Hz), 2.35 (6H,s), 3.54(2H,m), 3.71(2H,m), 4.00(3H,s), 5.29 (1H,s), 7.3–7.6(3H,m), 8.16(1H,s).

MIC against P. Mirabilis 889 is 0.25 μg ml$^{-1}$.

I claim:
1. A compound of the formula (I):

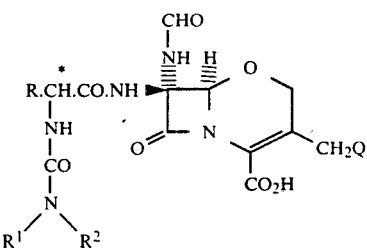

a pharmaceutically acceptable salt thereof or an in-vivo hydrolyzable ester thereof wherein R is phenyl unsubstituted or substituted by up to three substituents selected from the group consisting of alkyl of 1 to 6 carbon atoms, phenyl, halo, alkoxy of 1 to 6 carbon atoms, amino, nitro, hydroxy, alkylamido of 1 to 6 carbon atoms, alkylcarbonyloxy of 1 to 6 carbon atoms, carboxy, alkoxycarbonyl of 1 to 6 carbon atoms, haloalkyl of 1 to 6 carbon atoms, oxoalkyl of 1 to 6 carbon atoms, alkylcarbonyl of 1 to 6 carbon atoms, alkylamino of 1 to 6 carbon atoms and dialkylamino of 1 to 6 carbon atoms in each alkyl moiety, or cycloalkyl of 3 to 6 carbon atoms, cyclohexenyl or cyclohexadienyl;

Q is acetoxy, carbamoyloxy, S-Het or a pyridinium moiety unsubstituted or substituted by one or two moieties selected from the group consisting of alkyl of 1 to 6 carbon atoms, alkoxy of 1 to 6 carbon atoms, hydroxyalkyl of 1 to 6 carbon atoms, alkenyl of up to 6 carbon atoms, alkoxyalkyl of 1 to 6 carbon atoms in each of the alkoxy and alkyl moieties, carboxyalkyl of 1 to 6 carbon atoms, sulphonyalky of 1 to 6 carbon atoms, carbamoylmethyl, carbamoyl, trifluoromethyl, hydroxy, halo and aminoalkyl of 1 to 6 carbon atoms;

Het is a imidazolyl, triazolyl, tetrazolyl, thiazolyl, thiadiazolyl, thiatriazolyl, oxazolyl, triazinyl, oxadiazolyl, 1-methyl-1-H-tetrazol-5-ylthio, 2-methyl-1,3,4,-thiadiazol-5-ylthio, 1-carboxymethyl-1H-tetrazol-5-ylthio or (6-hydroxy-2-methyl-5-oxo-2H-1,2,4-triazin-3ylthio;

and $R^1$ and $R^2$ together with a nitrogen atom to which they are attached form a 5- or 6-membered hetertocyclic ring containing one or two nitrogen heteroatoms unsubstituted or substituted by alkyl of 1 to 6 carbon atoms, alkenyl of up to 6 carbon atoms, alkynyl of up to 6 carbon atoms, cycloalkyl of 3 to 6 carbon atoms, cycloalkenyl of 3 to 6 carbon atoms, phenyl, oxo, hydroxy or hydroxy substituted by a substituent selected from the group consisting of alkyl of 1 to 6 carbon atoms, of up to 6 carbon atoms, cycloalkyl of 3 to 6 carbon atoms, phenyl, pyridyl, pyrimidyl and benzyl; mercapto, alkylsulphonyl of 1 to 6 carbon atoms, alkenylamino of up to 6 carbon atoms, cycloalkylamino of 3 to 6 carbon atoms, phenylamino or benzylamino.

2. A compound according to claim 1 wherein R is phenyl, 4-hydroxyphenyl, 3,4-dialkylcarbonyloxyphenyl of 1 to 6 carbon atoms in each alkyl moiety, 3,4-dihydroxyphenyl, 2-thienyl, 3-thienyl or 2-amino-4-thiazolyl.

3. A compound of the formula (II):

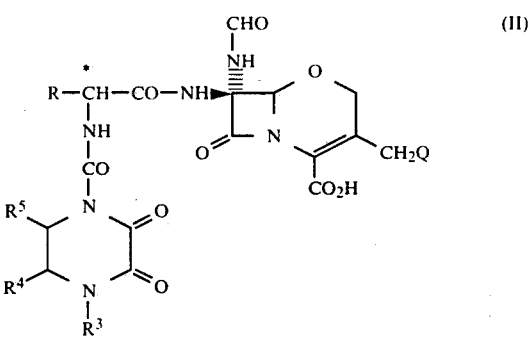

a pharmaceutically acceptable salt thereof or an in-vivo hydrolyzable ester thereof wherein R is phenyl unsubstituted or substituted by up to three substituents selected from the group consisting of alkyl of 1 to 6 carbon atoms, phenyl, halo, alkoxy of 1 to 6 carbon atoms, amino, nitro, hydroxy, alkylamido of 1 to 6 carbon atoms, alklcarbonyloxy of 1 to 6 carbon atoms, carboxy, alkoxycarbonyl of 1 to 6 carbon atoms, haloalkyl of 1 to 6 carbon atoms, oxoalkyl of 1 to 6 carbon atoms, alkylcarbonyl of 1 to 6 carbon atoms, alkylamino of 1 to 6 carbon atoms and dialkylamino of 1 to 6 carbon atoms, cyclohexenyl or cyclohexadienyl Q is acetoxy, carbamoyloxy, S-Het or a pyridinium moiety unsubstituted or substituted by one or two moieties selected from the group consisting of alkyl of 1 to 6 carbon atoms, alkoxy of 1 to 6 carbon atoms, hydroxyalkyl of 1 to 6 carbon atoms, alkenyl of up to 6 carbon atoms, alkoxyalkyl of 1 to 6 carbon atoms in each of the alkoxy and alkyl moieties, carboxyalkyl of 1 to 6 carbon atoms, sulphonyalkyl of 1 to 6 carbon atoms, carbamoylmethyl, carbamoyl, trifluormethyl, hydroxy, halo and aminoalkyl of 1 to 6 carbon atoms;

Het is imidazolyl, triazolyl, tetrazolyl, thiazolyl, thiadiazolyl, thiatriazolyl, oxazolyl, triazinyl, oxadiazolyl, 1-methyl-1-H-tetrazol-5-ylthio, 2-methyl-1,3,4-thiadiazolyl, thiatriazolyl, oxazolyl, triazinyl, oxadiazolyl, 1-methyl-1-H-tetrazol-5-ylthio, 2-methyl-1,3,4,-thiadiazol-5-ylthio, 1-carboxymethyl-1H-tetrazol-5-ylthio or 6-hydroxy-2-methyl-5-oxo-2H-1,2,4-triazin-3-ylthio;

R³ is hydrogen, alkyl of 1 to 6 carbon atoms, aryl or aralkyl; and

R⁴ and R⁵ are the same or different and each is hydrogen, alkyl of 1 to 6 carbon atoms, halo, amino, hydroxy or alkoxy of 1 to 6 carbon atoms.

4. A compound which is

7β-[2-[(4-ethyl-2,3-dioxopiperazin-1-yl) carbonylamino]-2((3,4-dihydroxyphenyl) acetamido-7α-formamido-3-[(1-methyl-1H-tetrazol-5-yl)thiomethyl]-1-oxadethiaceph-3-em-4-carboxylic acid;

7β-[2-(3,4-diacetoxyphenyl)-2[(4-ethyl-2,3-dioxopiperazin-1-yl) carbonylamino]acetamido]-7α-formamido-3[(1-methyl-1H-tetrazol-5-yl) thiomethyl]-1-oxadethia-ceph-3-em-4-carboxylic acid;

7β-[2-(4-ethyl-2,3-dioxopiperazin-1-yl]-carbonylamino)-2-phenylacetamido]-7α-formamido-3[1-methyl-1H-tetrazol-5-yl)-thiomethyl]-1-oxadethia-ceph-3-em-4-carboxylic acid;

7β-[D-2-[(4-ethyl-2,3-dioxopiperazin-1-yl) carbonylaminoamino]-2(3,4-dihydroxyphenyl) acetamido]-7α-formamido-3-[(1-methyl-1H-tetrazol-5-yl) thiomethyl]-1-oxadethia-ceph-3-em-4-carboxylic acid;

7β-[D-2-(3,4-diacetoxyphenyl)-2[(4-ethyl-2,3-dioxopiperazin-1-yl)carbonylamino]acetamido]-7α-formamido-3[(1-methyl-1H-tetrazol-5-yl) thiomethyl]-1-oxadethia-ceph-3-em-4-carboxylic acid; or 7β-[D-2-[(4-ethyl-2,3-dioxopiperazin-1-yl]carbonylamino)-2-phenylacetamido]7αformamido-3[(1-methyl-1H-tetrazol-5-yl)-thiomethyl]-1-oxadethia-ceph-3-em-4-carboxylic acid;

or a pharmaceutically acceptable salt thereof or an in-vivo hydrolyzable ester thereof.

5. A pharmaceutical composition useful for treating bacterial infections in humans and animals which comprises an antibacterially effective amount of a compound of the formula (I):

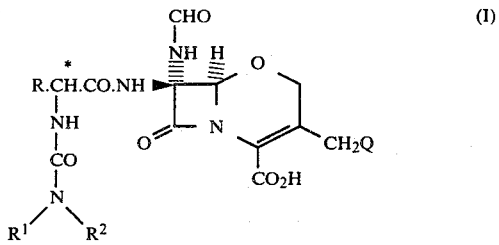

(I)

a pharmaceutically acceptable salt thereof or an in-vivo hydrolyzable ester thereof wherein R is phenyl unsubstituted or substituted by up to three substituents selected from the group consisting of alkyl of 1 to 6 carbon atoms, phenyl, halo, alkoxy of 1 to 6 carbon atoms, amino, nitro, hydroxy, alkylamido of 1 to 6 carbon atoms, alkylcarbonyloxy of 1 to 6 carbon atoms, carboxy, alkoxycarbonyl of 1 to 6 carbon atoms, haloalkyl of 1 to 6 carbon atoms, oxoalkyl of 1 to 6 carbon atoms, alkylcarbonyl of 1 to 6 carbon atoms, alkylamino of 1 to 6 carbon atoms and dialkylamino of 1 to 6 carbon atoms in each alkyl moiety, or cycloalkyl of 3 to 6 carbon atoms, cyclohexenyl or cyclohexadienyl;

Q is acetoxy, carbamoyloxy, S-Het or a pyridinium moiety unsubstituted or substituted by one or two moieties selected from the group consisting of alkyl of 1 to 6 carbon atoms, alkoxy of 1 to 6 carbon atoms, hydroxyalkyl of 1 to 6 carbon atoms, alkenyl of up to 6 carbon atoms, alkoxyalkyl of 1 to 6 carbon atoms in each of the alkoxy and alkyl moieties, carboxyalkyl of 1 to 6 carbon atoms, sulphonyalkyl of 1 to 6 carbon atoms, carbamoylmethyl, carbamoyl, trifluoromethyl, hydroxy, halo and aminoalkyl of 1 to 6 carbon atoms;

Het is imidazolyl, triazolyl, tetrazolyl, thiazolyl, thiadiazolyl, thiatriazolyl, oxazolyl, triazinyl, oxadiazolyl, 1-methyl-1H-tetrazol-5-ylthio, 2-methyl-1,3,4,-thiadiazol-5-ylthio, 1-carboxymethyl-1H-tetrazol-5-ylthio or 6-hydroxy-2-methyl-5-oxo- 2H-1,2,4-triazin-3-ylthio;

and R¹ and R² together with a nitrogen atom to which they are attached form a 5- or 6-membered hetertocyclic ring containing one or two nitrogen heteroatoms unsubstituted or substituted by alkyl of 1 to 6 carbon atoms, alkenyl of up to 6 carbon atoms, alkynyl of up to 6 carbon atoms, cycloalkyl of 3 to 6 carbon atoms, cycloalkenyl of 3 to 6 carbon atoms, phenyl, oxo, hydroxy or hydroxy substituted by a substituent selected from the group consisting of alkyl of 1 to 6 carbon atoms, alkenyl of up to 6 carbon atoms, cycloalkyl of 3 to 6 carbon atoms, phenyl, pyridyl, pyrimidyl and benzyl; mercapto, alkylsulphonyl of 1 to 6 carbon atoms, alkenylamino of up to 6 carbon atoms, cycloalkylamino of 3 to 6 carbon atoms, phenylamino or benzylamino, in combination with a pharmaceutically acceptable carrier.

6. A composition according to claim 5 wherein R is phenyl, 4-hydroxyphenyl, 3,4-dialkylcarbonyloxyphenyl of 1 to 6 carbon atoms in each alkyl moiety, 3,4-dihydroxyphenyl, 2-thienyl, 3-thienyl or 2-amino-4-thiazolyl.

7. A pharmaceutical composition useful for treating bacterial infections in humans and animals which comprises an antibacterially effective amount of a compound of the formula (II):

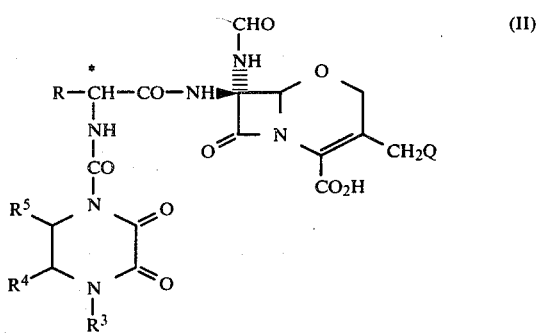

(II)

a pharmaceutically acceptable salt thereof or an in-vivo hydrolyzable ester thereof wherein R is phenyl unsubstituted or substituted by up to three substituents selected from the group consisting of alkyl of 1 to 6 carbon atoms, phenyl, halo, alkoxy of 1 to 6 carbon atoms, amino, nitro, hydroxy, alkylamido of 1 to 6 carbon atoms, alkylcarbonyloxy of 1 to 6 carbon atoms, carboxy, alkoxycarbonyl of 1 to 6 carbon atoms, haloalkyl of 1 to 6 carbon atoms, oxoalkyl of 1 to 6 carbon atoms, alkylcarbonyl of 1 to 6 carbon atoms, alkylamino of 1 to 6 carbon atoms and dialkylamino of 1 to 6 carbon atoms, cyclohexenyl or cyclohexadienyl;

Q is acetoxy, carbamoyloxy, S-Het or a pyridinium moiety unsubstituted or substituted by one or two moieties selected from the group consisting of alkyl of 1 to 6 carbon atoms, alkoxy of 1 to 6 carbon atoms, hydroxyalkyl of 1 to 6 carbon atoms, alkenyl of up to 6 carbon atoms, alkoxyalkyl of 1 to 6 carbon atoms in each of the alkoxy and alkyl moieties, carboxyalkyl of 1 to 6 carbon atoms, sulphonyalkyl of 1 to 6 carbon atoms, carbamoylmethyl, carbamoyl, trifluormethyl, hydroxy, halo and aminoalkyl of 1 to 6 carbon atoms;

Het is imidazolyl, triazolyl, tetrazolyl, thiazolyl, thiadiazolyl, thiatriazolyl, oxazolyl, triazinyl, oxadiazolyl, 1-methyl-1H-tetrazol-5-ylthio, 2-methyl-1,3,4,-thiadiazol-5-ylthio, 1-carboxymethyl-1H-tetrazol-5-ylthio or 6-hydroxy-2-methyl-5-oxo-2H-1,2,4-triazin-3-ylthio;

$R^3$ is hydrogen, alkyl of 1 to 6 carbon atoms, aryl or aralkyl; and $R^4$ and $R^5$ are the same or different and each is hydrogen, alkyl of 1 to 6 carbon atoms, halo, amino, hydroxy or alkoxy of 1 to 6 carbon atoms, in combination with a pharmaceutically acceptable carrier.

8. A method of treating bacterial infections in humans and animals which comprises administering to a human or animal in need thereof an antibacterially effective amount of a compound of the formula (I):

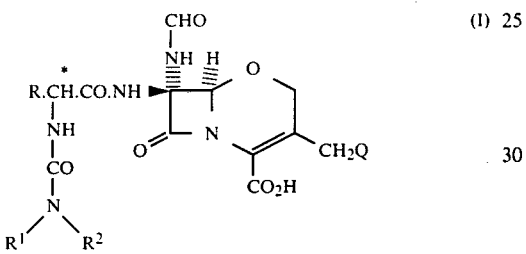

a pharmaceutically acceptable salt thereof or an in-vivo hydrolyzable ester thereof wherein R is phenyl unsubstituted or substituted by up to three substituents selected from the group consisting of alkyl of 1 to 6 carbon atoms, phenyl, halo, alkoxy of 1 to 6 carbon atoms, amino, nitro, hydroxy, alkylamido of 1 to 6 carbon atoms, alkylcarbonyloxy of 1 to 6 carbon atoms, carboxy, alkoxycarbonyl of 1 to 6 carbon atoms, haloalkyl of 1 to 6 carbon atoms, oxoalkyl of 1 to 6 carbon atoms, alkylcarbonyl of 1 to 6 carbon atoms, alkylamino of 1 to 6 carbon atoms and dialkylamino of 1 to 6 carbon atoms in each alkyl moiety, or cycloalkyl of 3 to 6 carbon atoms, cyclohexenyl or cyclohexadienyl;

Q is acetoxy, carbamoyloxy, S-Het or a pyridinium moiety unsubstituted or substituted by one or two moieties selected from the group consisting of alkyl of 1 to 6 carbon atoms, alkoxy of 1 to 6 carbon atoms, hydroxyalkyl of 1 to 6 carbon atoms, alkenyl of up to 6 carbon atoms, alkoxyalkyl of 1 to 6 carbon atoms in each of the alkoxy and alkyl moieties, carboxyalkyl of 1 to 6 carbon atoms, sulphonyalkyl of 1 to 6 carbon atoms, carbamoylmethyl, carbamoyl, trifluoromethyl, hydroxy, halo and aminoalkyl of 1 to 6 carbon atoms;

Het is imidazolyl, triazolyl, tetrazolyl, thiazolyl, thiadiazolyl, thiatriazolyl, oxazolyl, triazinyl, oxadiazolyl, 1-methyl-1H-tetrazol-5-ylthio, 2-methyl-1,3,4,-thiadiazol-5-ylthio, 1-carboxymethyl-1H-tetrazol-5-ylthio or 6-hydroxy-2-methyl-5-oxo-2H-1,2,4-triazin-3-ylthio;

and $R^1$ and $R^2$ together with a nitrogen atom to which they are attached form a 5- or 6-membered hetertocyclic ring containing one or two nitrogen heteroatoms unsubstituted or substituted by alkyl of 1 to 6 carbon atoms, alkenyl of up to 6 carbon atoms, alkynyl of up to 6 carbon atoms, cycloalkyl of 3 to 6 carbon atoms, cycloalkenyl of 3 to 6 carbon atoms, phenyl, oxo, hydroxy hydroxy substituted by a substituent selected from the group consisting of 1 to 6 carbon atoms, alkenyl of up to 6 carbon atoms, cycloalkyl of 3 to 6 carbon atoms, phenyl, pyridyl, pyrimidyl and benzyl; mercapto, alkylsulphonyl of 1 to 6 carbon atoms, alkenylamino of up to 6 carbon atoms, cycloalkylamino of 3 to 6 carbon atoms, phenylamino or benzylamino, in combination with a pharmaceutically acceptable carrier.

9. A method according to claim 8 wherein R is phenyl, 4-hydroxyphenyl, 3,4-dialkylcarbonyloxyphenyl of 1 to 6 carbon atoms in each alkyl moiety, 3,4-dihydroxyphenyl, 2-thienyl, 3-thienyl or 2-amino-4-thiazolyl.

10. A method of treating bacterial infections in humans and animals which comprises administering to a human or animal in need thereof an antibacterially effective amount of a compound of the formula (II):

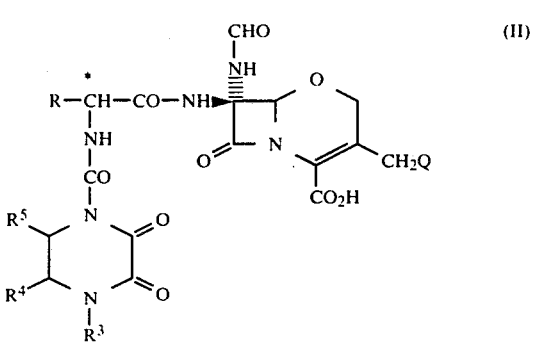

a pharmaceutically acceptable salt thereof or an in-vivo hydrolyzable ester thereof wherein R is phenyl unsubstituted or substituted by up to three substituents selected from the group consisting of alkyl of 1 to 6 carbon atoms, phenyl, halo, alkoxy of 1 to 6 carbon atoms, amino, nitro, hydroxy, alkylamido of 1 to 6 carbon atoms, alkylcarbonyloxy of 1 to 6 carbon atoms, carboxy, alkoxycarbonyl of 1 to 6 carbon atoms, haloalkyl of 1 to 6 carbon atoms, oxoalkyl of 1 to 6 carbon atoms, alkylcarbonyl of 1 to 6 carbon atoms, alkylamino of 1 to 6 carbon atoms and dialkylamino of 1 to 6 carbon atoms, cyclohexenyl or cyclohexadienyl;

Q is acetoxy, carbamoyloxy, S-Het or a pyridinium moiety unsubstituted or substituted by one or two moieties selected from the group consisting of alkyl of 1 to 6 carbon atoms, alkoxy of 1 to 6 carbon atoms, hydroxyalkyl of 1 to 6 carbon atoms, alkenyl of up to 6 carbon atoms, alkoxyalkyl of 1 to 6 carbon atoms in each of the alkoxy and alkyl moieties, carboxyalkyl of 1 to 6 carbon atoms, sulphonyalkyl of 1 to 6 carbon atoms, carbamoylmethyl, carbamoyl, trifluormethyl, hydroxy, halo and aminoalkyl of 1 to 6 carbon atoms;

Het is imidazolyl, triazolyl, tetrazolyl, thiazolyl, thiadiazolyl, thiatriazolyl, oxazolyl, triazinyl, oxadiazolyl, 1-methyl-1H-tetrazol-5-ylthio, 2-methyl-1,3,4,-thiadriazol-5 -ylthio, 1-carboxymethyl-1H-tetrazol-5-ylthio or 6-hydroxy-2 -methyl-5-oxo-2H-1,2,4-triazin-3-ylthio;

R[3] is hydrogen, alkyl of 1 to 6 carbon atoms, aryl or aralkyl; and

R[4] and R[5] are the same or different and each is hydrogen, alkyl of 1 to 6 carbon atoms, halo, amino, hydroxy or alkoxy of 1 to 6 carbon atoms, in combination with a pharmaceutically acceptable carrier.

11. A pharmaceutical composition useful for treating bacterial infections in humans and animals which comprises an antibacterially effective amount of 7β-[2-[(4-ethyl-2,3-dioxopiperazin-1-yl)carbonylamino]-2(3,4-dihydroxyphenyl)acetamido-7α-formamido-3-[(1-methyl-1H-tetrazol-5-yl)thiomethyl]-1-oxadethiaceph-3-em-4-carboxylic acid;

7β-[2-(3,4-diacetoxyphenyl)-2[(4-ethyl-2,3-dioxopiperazin-1-yl) carbonylamino]acetamido]-7α-formamido-3[(1-methyl-1H-tetrazol-5-yl)thiomethyl]-1-oxadethia-ceph-3-em-4-carboxylic acid;

7β-[2-([4-ethyl-2,3-dioxopiperazin-1-yl]-carbonylamino)-2phenylacetamido]-7α-formamido-3[1-methyl-1H-tetrazol-5-yl)-thiomethyl]-1-oxadethia-ceph-3-em-4-carboxylic acid;

7β-[D-2-[(4-ethyl-2,3-dioxopiperazin-1-yl)-carbonylamino]-2(3,4-dihydroxyphenyl)acetamido]-7α-formamido-3-[(1-methyl-1H-tetrazol-5-yl)thiomethyl]-1-oxadethia-ceph-3-em-4-carboxylic acid;

7β-[D-2-[(3,4-diacetoxyphenyl)-2[(4-ethyl-2,3-dioxopiperazin-1-yl)carbonylamino]acetamido]-7α-formamido-3[(1-methyl-1H-tetrazol-5-yl)thiomethyl]-1-oxadethia-ceph-3-em-4-caboxylic acid; or 7β-[D-2[(4-ethyl-2,3-dioxopiperazin-1-yl]-carbonylamino)-2-phenylacetamido]-7α-formamido-3[(1-methyl-1H-tetrazol-5-yl)-thiomethyl]-1-oxadethia-ceph-3-em-4-carboxylic acid;

or a pharmaceutically acceptable salt thereof or an in-vivo hydrolyzable ester thereof, in combination with a pharmaceutically acceptable carrier.

12. A method of treating bacterial infections in humans and animals which comprises administering to a human or animal in need thereof an antibacterially effective amount of 7β-[2-[(4-ethyl-2,3-dioxopiperazin-1-yl)carbonylamino]-2(3,4-dihydroxyphenyl)acetamido-7α-formamido-3-[(1-methyl-1H-teterazol-5-yl)thiomethyl]-1-oxadethiaceph-3-em-4-carboxylic acid;

7β-[2-(3,4-diacetoxyphenyl)-2[(4-ethyl-2,3-dioxopiperazin-1-yl)carbonylamino]acetamido]-7α-formamido-3[(1-methyl-1H-tetrazol-5-yl)thiomethyl]-1-oxadethia-ceph-3-em-4-carboxylic acid;

7β-[2-([4-ethyl-2,3-dioxopiperazin-1-yl]-carbonylamino)-2-phenylacetamido]-7α-formamido-3[1-methyl-1H-tetrazol-5-yl)-thiomethyl]-1-oxadethia-ceph-3-em-4-carboxylic acid;

7β-[D-2-[(4-ethyl-2,3-dioxopiperazin-1-yl)-carbonylamino]-2(3,4-dihydroxyphenyl)acetamido]-7α-formamido-3-[1-methyl-1H-tetrazol-5-yl)thiomethyl]-1-oxadethia-ceph-3-em-4-carboxylic acid;

7β-[D-2-(3,4-diacetoxyphenyl)-2(4-ethyl-2,3-dioxopiperazin-1-yl)carbonylamino]acetamido]-7α-formamido-3[(1-methyl-1H-teterazol-5-yl) thiomethyl]-1-oxadethia-ceph-3-em-4-carboxylic acid; or 7β-[D-2-[(4-ethyl-2,3-dioxopiperazin-1-yl]-carbonylamino)-2-phenylacetamido]-7α-formamido-3[(1-methyl-1H-tetrazol-5-yl)-thiomethyl]-1-oxadethia-ceph-3-em-4-carboxylic acid;

or a pharmaceutically acceptable salt thereof or an in-vivo hydrolyzable ester thereof, in combination with a pharmaceutically acceptable carrier.

* * * * *